US00PP24521P2

(12) United States Plant Patent
Sakazaki

(10) Patent No.: US PP24,521 P2
(45) Date of Patent: Jun. 3, 2014

(54) ***PETUNIA* PLANT NAMED 'USTUN47601'**

(50) Latin Name: *Petunia×hybrida*
Varietal Denomination: USTUN47601

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 83 days.

(21) Appl. No.: 13/507,526

(22) Filed: Jul. 5, 2012

(51) Int. Cl.
*A01H 5/00* (2006.01)

(52) U.S. Cl.
USPC ..... Plt./356.21; Plt./356.1; Plt./356.11; Plt./356.23

(58) Field of Classification Search
USPC ..... Plt./356.1, 356.11, 356.21, 356.23
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'USTUN47601', characterized by its upright to outwardly spreading and low mounding plant habit; freely branching habit; vigorous growth habit; early and freely flowering habit; medium-sized coral red-colored flowers; and good garden performance.

1 Drawing Sheet

Botanical designation: *Petunia×hybrida*.
Cultivar denomination: 'USTUN47601'.

BACKGROUND OF THE INVENTION

The present invention relates to a new and distinct cultivar of *Petunia* plant, botanically known as *Petunia×hybrida* and hereinafter referred to by the name 'USTUN47601'.

The new *Petunia* plant is a product of a planned breeding program conducted by the Inventor in Higashiomi, Shiga, Japan and Bonsall, Calif. The objective of the breeding program is to create new freely-branching and mounding *Petunia* plants with early and freely flowering habit, attractive medium-sized flowers and good garden performance.

The new *Petunia* plant originated from a cross-pollination made by the Inventor on May 6, 2009 in Higashiomi, Shiga, Japan of a proprietary seedling selection of *Petunia×hybrida* identified as code number 08P357-02, not patented, as the female, or seed, parent with a proprietary seedling selection of *Petunia×hybrida* identified as code number 09PJ23, not patented, as the male, or pollen, parent. The new *Petunia* plant was discovered and selected by the Inventor as a single flowering plant within the progeny of the stated cross-pollination in a controlled environment in Bonsall, Calif. on May 27, 2010.

Asexual reproduction of the new *Petunia* plant by vegetative cuttings in a controlled greenhouse environment in Bonsall, Calif. since May 28, 2010 has shown that the unique features of this new *Petunia* plant are stable and reproduced true to type in successive generations.

SUMMARY OF THE INVENTION

Plants of the new *Petunia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'USTUN47601'. These characteristics in combination distinguish 'USTUN47601' as a new and distinct *Petunia* plant:

1. Upright to outwardly spreading and low mounding plant habit.
2. Freely branching habit.
3. Vigorous growth habit.
4. Early and freely flowering habit.
5. Medium-sized coral red-colored flowers.
6. Good garden performance.

Plants of the new *Petunia* can be compared to plants of the female parent selection. In side-by-side comparisons conducted in Bonsall, Calif., plants of the new *Petunia* differ from plants of the female parent selection in the following characteristics:

1. Plants of the new *Petunia* have slightly smaller flowers than plants of the female parent selection.
2. Plants of the new *Petunia* and the female parent selection differ in flower color as plants of the female parent selection have darker-colored flowers.

Plants of the new *Petunia* can be compared to plants of the male parent selection. In side-by-side comparisons conducted in Bonsall, Calif., plants of the new *Petunia* differ from plants of the male parent selection in the following characteristics:

1. Plants of the new *Petunia* are more mounding than plants of the male parent selection.
2. Plants of the new *Petunia* have larger flowers than plants of the male parent selection.
3. Plants of the new *Petunia* and the male parent selection differ in flower color as plants of the male parent selection have lighter-colored flowers.

Plants of the new *Petunia* can be compared to plants of 'USTUN19603', disclosed in U.S. Plant Pat. No. 21,675. In side-by-side comparisons conducted in Bonsall, Calif., plants of the new *Petunia* differed from plants of 'USTUN19603' in the following characteristics:

1. Plants of the new *Petunia* had larger flowers than plants of 'USTUN19603'.

2. Plants of the new *Petunia* and 'USTUN19603' differed in flower color as plants of 'USTUN19603' had bright pink-colored flowers.

Plants of the new *Petunia* can also be compared to plants of 'USTUN34803', disclosed in U.S. Plant Pat. No. 22,884. In side-by-side comparisons, plants of the new *Petunia* differed from plants of 'USTUN34803' in the following characteristics:

1. Plants of the new *Petunia* had larger flowers than plants of 'USTUN34803'.
2. Plants of the new *Petunia* and 'USTUN34803' differed in flower color as plants of 'USTUN34803' had red purple-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'USTUN47601' grown in a container.

The photograph at the top of the sheet is a close-up view of typical flowers of 'USTUN47601'.

DETAILED BOTANICAL DESCRIPTION

The aforementioned photographs and following observations, measurements and values describe plants grown during the spring in 11.4-cm containers in a polyethylene-covered greenhouse and finished in an outdoor nursery in Bonsall, Calif. During the production of the plants, day temperatures averaged 24° C. and night temperatures averaged 18° C. Plants were pinched one time at planting and were eight weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN47601'.

Parentage:

*Female, or seed, parent.*—Proprietary seedling selection of *Petunia×hybrida* identified as code number 08P357-02, not patented.

*Male, or pollen, parent.*—Proprietary seedling selection of *Petunia×hybrida* identified as code number 09PJ23, not patented.

Propagation:

*Type.*—Terminal vegetative cuttings.

*Time to initiate roots, summer.*—About three days at temperatures ranging from 17° C. to 29° C.

*Time to initiate roots, winter.*—About four days at temperatures ranging from 17° C. to 21° C.

*Time to produce a rooted plant, summer.*—About 15 days at temperatures ranging from 17° C. to 29° C.

*Time to produce a rooted plant, winter.*—About 20 days at temperatures ranging from 17° C. to 21° C.

*Root description.*—Medium in thickness, fibrous; white in color.

*Rooting habit.*—Freely branching; medium density.

Plant description:

*Plant and growth habit.*—Upright to outwardly spreading and low mounding plant habit; freely branching habit with about 25 primary lateral branches with multiple secondary lateral branches developing per plant; dense and bushy appearance; pinching enhances development of lateral branches; vigorous growth habit.

*Plant height.*—About 12.5 cm.

*Plant diameter (area of spread).*—About 30 cm.

*Lateral branches.*—Length: About 15.5 cm. Diameter: About 3 mm. Internode length: About 1.3 cm. Strength: Strong. Texture: Pubescent. Color: Close to 146D.

Foliage description:

*Arrangement.*—Alternate before flowering; opposite after flowers develop; simple.

*Length.*—About 3.4 cm.

*Width.*—About 1.6 cm.

*Shape.*—Elliptical.

*Apex.*—Acute.

*Base.*—Attenuate.

*Margin.*—Entire.

*Texture, upper and lower surfaces.*—Sparsely pubescent.

*Venation pattern.*—Pinnate, arcuate.

*Color.*—Developing leaves, upper surface: Close to 137A. Developing leaves, lower surface: Close to 137C. Fully expanded leaves, upper surface: Close to 137A; venation, close to 146B. Fully expanded leaves, lower surface: Close to 146B; venation, close to 146B.

*Petioles.*—Length: About 1 cm. Diameter: About 2 mm. Texture, upper and lower surfaces: Sparsely pubescent. Color, upper and lower surfaces: Close to 146C.

Flower description:

*Flower type and habit.*—Single axillary salverform flowers; flowers face mostly upward to outwardly; freely flowering habit with about 19 to 20 flower buds and open flowers developing per lateral branch.

*Natural flowering season.*—Long day responsive; long flowering period, plants flower from early spring until frost in the autumn, flowering continuous during this period; early flowering habit, plants begin flowering about eight weeks after planting.

*Flower longevity on the plant.*—About three to four days; flowers persistent.

*Fragrance.*—None detected.

*Flower size.*—Diameter: About 3.2 cm. Depth (height): About 3.6 cm. Throat diameter, distal: About 6 mm. Tube length: About 2.8 cm. Tube diameter, proximal: About 3 mm.

*Flower buds.*—Length: About 3 cm. Diameter: About 5 mm. Shape: Elongated oblong. Color: Close to 176B.

*Petals.*—Quantity and arrangement: Five petals fused in a single salverform whorl. Petal lobe length (from throat): About 1.5 cm. Petal lobe width: About 1.4 cm. Petal lobe shape: Roughly obovate. Petal lobe apex: Rounded. Petal lobe margin: Entire. Petal lobe texture, upper and lower surfaces: Smooth, glabrous; velvety. Throat texture: Smooth, glabrous. Tube texture: Pubescent. Color: When opening and fully opened, upper surface: Close to 46A; venation, close to 46A; color does not fade with development. When opening and fully opened, lower surface: Close to 182B; venation, close to 183D. Flower throat:

Slightly more grey than 76A; venation, close to 183C. Flower tube (outside): Lighter than N77D and towards the base, close to 145C; venation, close to 183C and towards the base, close to 145B.

*Sepals.*—Quantity and arrangement: Five sepals fused in a single star-shaped whorl. Length: About 1.3 cm. Width: About 2 mm. Shape: Lanceolate. Apex: Rounded. Margin: Entire. Texture, upper and lower surfaces: Pubescent. Color, upper surface: Close to 146A. Color, lower surface: Close to 146A to 146B.

*Peduncles.*—Length: About 2.2 cm. Width: About 1.5 mm. Angle: About 30° from the stem axis. Strength: Strong. Texture: Pubescent. Color: Close to 144A.

*Reproductive organs.*—Stamens: Quantity per flower: Five. Filament length: About 1.5 cm. Filament color: Close to 145D. Anther length: About 2 mm. Anther shape: Rounded. Anther color: Close to 158A. Pollen amount: Scarce. Pollen color: Close to 158D. Pistils: Quantity per flower: One. Pistil length: About 1.9 cm. Style length: About 1.4 cm. Style color: Close to 145C. Stigma shape: Rounded. Stigma color: Close to 146A. Ovary color: Close to 146D.

*Seeds and fruits.*—Seed and fruit development has not been observed on plants of the new *Petunia.*

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'USTUN47601' as illustrated and described.

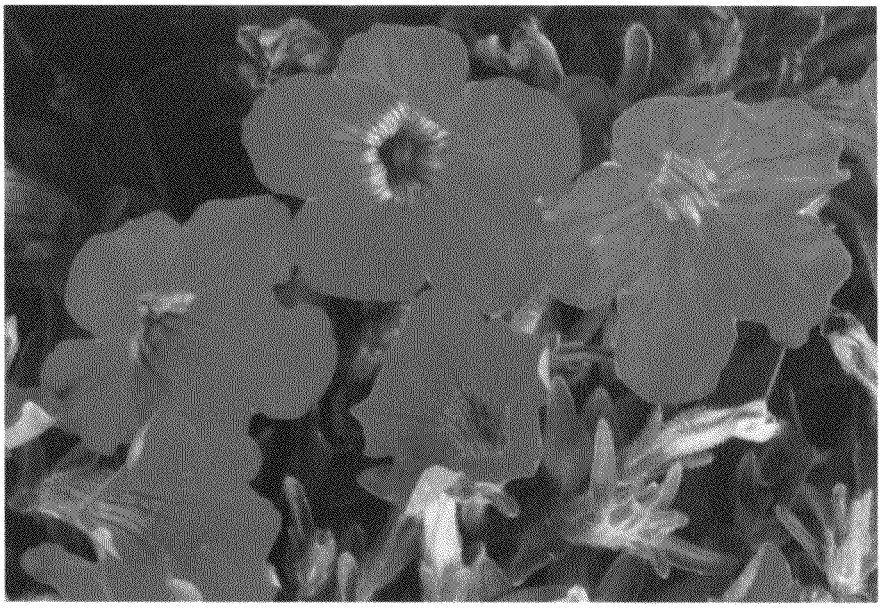
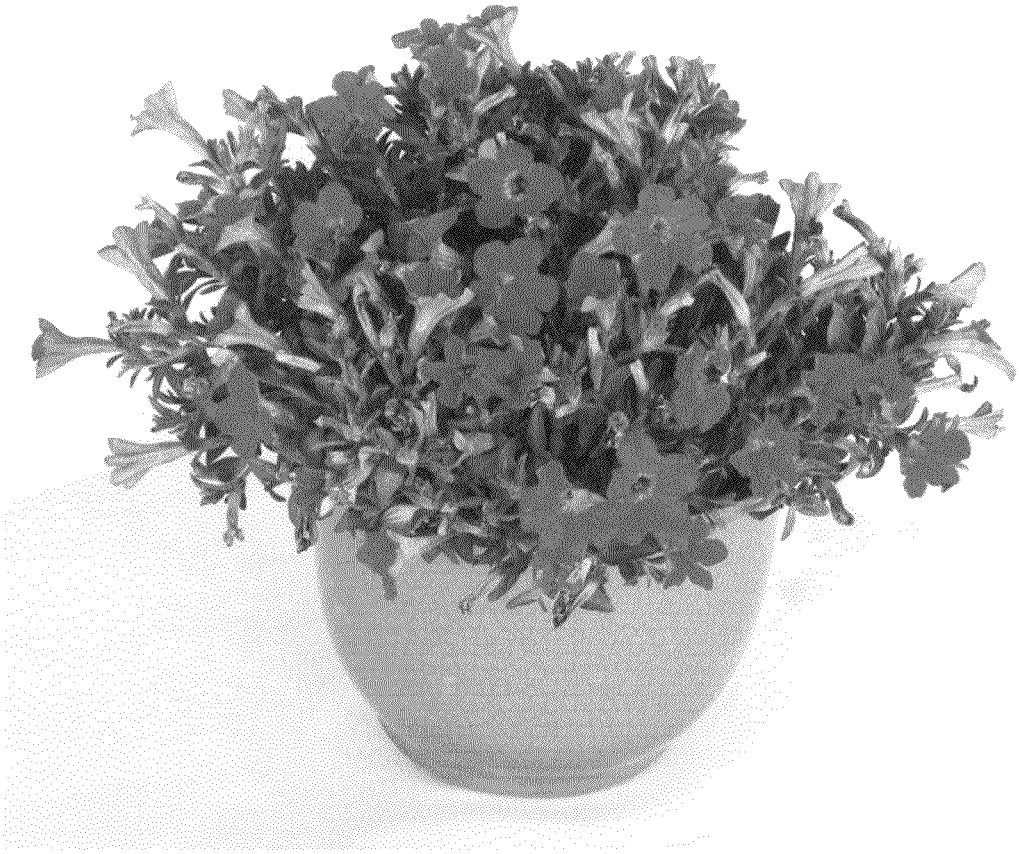

* * * * *